United States Patent
Hart et al.

(10) Patent No.: US 10,603,102 B2
(45) Date of Patent: Mar. 31, 2020

(54) LIMITED-USE SURGICAL DEVICES

(71) Applicant: COVIDIEN LP, Mansfield, MA (US)

(72) Inventors: Keir Hart, Lafayette, CO (US); Jeffrey R. Townsend, Longmont, CO (US); Weng-Kai K. Lee, Longmont, CO (US); Prakash Manley, Lafayette, CO (US); Geneva Ladtkow, Arvada, CO (US); Arlen J. Reschke, Longmont, CO (US); Diana Gunnarson, Longmont, CO (US); Scott N. Lacosta, Lafayette, CO (US); Kelley D. Goodman, Erie, CO (US); Kenneth E. Netzel, Loveland, CO (US); Susan Hiebert, Lyons, CO (US)

(73) Assignee: COVIDIEN LP, Mansfield, MA (US)

( * ) Notice: Subject to any disclaimer, the term of this patent is extended or adjusted under 35 U.S.C. 154(b) by 487 days.

(21) Appl. No.: 15/422,709

(22) Filed: Feb. 2, 2017

(65) Prior Publication Data

US 2017/0143407 A1 May 25, 2017

Related U.S. Application Data

(63) Continuation of application No. 14/258,127, filed on Apr. 22, 2014, now Pat. No. 9,566,109.
(Continued)

(51) Int. Cl.
*A61B 18/12* (2006.01)
*A61B 18/14* (2006.01)
(Continued)

(52) U.S. Cl.
CPC ...... *A61B 18/1442* (2013.01); *A61B 18/1445* (2013.01); *A61B 90/08* (2016.02);
(Continued)

(58) Field of Classification Search
CPC ............ A61B 18/1442; A61B 18/1445; A61B 2018/00178; A61B 2018/00666;
(Continued)

(56) References Cited

U.S. PATENT DOCUMENTS

| 1,996,258 A | 4/1935 | Ruskin |
| 2,051,169 A | 8/1936 | Handschug |

(Continued)

FOREIGN PATENT DOCUMENTS

| EP | 1779764 A1 | 5/2007 |
| EP | 2329783 A1 | 6/2011 |

(Continued)

OTHER PUBLICATIONS

European Search Report dated Feb. 3, 2017, issued in EP Application No. 14826713.
(Continued)

*Primary Examiner* — Daniel W Fowler
(74) *Attorney, Agent, or Firm* — Carter, DeLuca & Farrell LLP

(57) ABSTRACT

A system includes an energy source and a surgical device. The energy source has a receptacle configured to delivery energy to the surgical device through a receptacle. The surgical device is configured to deliver the energy to tissue. The surgical device includes a plug selectively engagable to the receptacle to couple the surgical device to the energy source. The plug includes a prong configured to mechanically transition from a condition permitting engagement of the plug and the receptacle to another condition inhibiting engagement of the plug with the receptacle upon reaching a predetermined usage threshold.

14 Claims, 12 Drawing Sheets

Related U.S. Application Data

(60) Provisional application No. 61/847,791, filed on Jul. 18, 2013.

(51) Int. Cl.
   *A61B 90/00* (2016.01)
   *A61B 18/00* (2006.01)

(52) U.S. Cl.
   CPC .............. *A61B 2018/00178* (2013.01); *A61B 2018/00666* (2013.01); *A61B 2018/00988* (2013.01); *A61B 2090/037* (2016.02); *A61B 2090/0803* (2016.02); *A61B 2090/0814* (2016.02)

(58) Field of Classification Search
   CPC .... A61B 2018/00988; A61B 2090/037; A61B 2090/0803; A61B 2090/0814
   See application file for complete search history.

(56) References Cited

U.S. PATENT DOCUMENTS

| | | | |
|---|---|---|---|
| 3,187,291 A * | 6/1965 | Hime | H01R 13/20 439/265 |
| 4,758,184 A | 7/1988 | Call | |
| 5,160,334 A | 11/1992 | Billings et al. | |
| 5,312,401 A | 5/1994 | Newton et al. | |
| 5,400,267 A | 3/1995 | Denen et al. | |
| 5,480,318 A * | 1/1996 | Garrison | H01R 13/20 439/102 |
| 5,611,798 A | 3/1997 | Eggers | |
| 5,630,726 A * | 5/1997 | Baldwin | H01R 13/20 439/270 |
| 5,688,269 A | 11/1997 | Newton et al. | |
| 5,830,212 A | 11/1998 | Cartmell et al. | |
| 6,063,075 A | 5/2000 | Mihori | |
| 6,190,385 B1 | 2/2001 | Tom et al. | |
| 6,203,541 B1 | 3/2001 | Keppel | |
| 6,237,604 B1 | 5/2001 | Burnside et al. | |
| 6,350,139 B1 | 2/2002 | Haag | |
| 6,409,722 B1 | 6/2002 | Hoey et al. | |
| 6,522,234 B1 | 2/2003 | Sturgill | |
| 6,537,272 B2 | 3/2003 | Christopherson et al. | |
| 6,644,986 B1 | 11/2003 | Wilker, Sr. | |
| 6,736,810 B2 | 5/2004 | Hoey et al. | |
| 6,849,073 B2 | 2/2005 | Hoey et al. | |
| 6,958,463 B1 | 10/2005 | Kochman et al. | |
| 7,041,096 B2 | 5/2006 | Malis et al. | |
| 7,169,144 B2 | 1/2007 | Hoey et al. | |
| 9,566,109 B2 | 2/2017 | Hart et al. | |
| 2005/0183656 A1 | 8/2005 | Isaacson et al. | |
| 2005/0239349 A9 | 10/2005 | Desinger | |
| 2005/0283148 A1 | 12/2005 | Janssen et al. | |
| 2007/0049914 A1 | 3/2007 | Eggleston | |
| 2009/0061667 A1 | 3/2009 | Grieff | |
| 2009/0065565 A1 | 3/2009 | Cao | |
| 2010/0136856 A1 | 6/2010 | Gleason et al. | |
| 2010/0280511 A1 | 11/2010 | Rachlin et al. | |
| 2011/0312207 A1 | 12/2011 | Chapel et al. | |
| 2013/0274734 A1 | 10/2013 | Maass et al. | |
| 2013/0289559 A1 | 10/2013 | Reid, Jr. | |

FOREIGN PATENT DOCUMENTS

| | | |
|---|---|---|
| EP | 2653126 A1 | 10/2013 |
| WO | 93/00862 A2 | 1/1993 |
| WO | 2005060365 A2 | 7/2005 |
| WO | 2005081730 A2 | 9/2005 |
| WO | 2007136694 A2 | 11/2007 |
| WO | 2012124831 A1 | 9/2012 |

OTHER PUBLICATIONS

International Preliminary Report on Patentability and Written Opinion of the International Searching Authority dated Jan. 19, 2016 for PCT/US2014/037820.

International Search Report dated Apr. 3, 2015, issued in PCT/US2014/037820.

\* cited by examiner

LIMITED-USE SURGICAL DEVICES

CROSS REFERENCE TO RELATED APPLICATIONS

The present application is a continuation of U.S. patent application Ser. No. 14/258,127, filed Apr. 22, 2014, which claims the benefit of and priority to U.S. Provisional Patent Application Ser. No. 61/847,791, filed Jul. 18, 2013. The entire contents of each of the above applications are hereby incorporated herein by reference.

BACKGROUND

Technical Field

The present disclosure relates to surgical devices and systems and, more particularly, to surgical devices and systems having a limited number of uses and/or period of use.

Background of Related Art

Certain surgical devices (or components thereof) are capable of being used multiple times, and are thus referred to as reusable devices (or reusable components), while other surgical devices (or components thereof) are configured for single use, and are thus referred to as disposable devices (or disposable components). Many such reusable and disposable surgical devices, and/or the components thereof, are designed for a pre-determined number of uses and/or for a pre-determined usage time. Use of these devices beyond their prescribed usage time or number of uses may result in failure of the device, damage to the device or surroundings, and/or injury to the patient or clinician. On the other hand, given the rising costs of performing medical procedures, clinician's have an incentive to maximize the reuse of surgical devices (or components thereof).

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

According to aspects of the present disclosure, a surgical instrument includes a plug having one or more prongs. The prong(s) has a first radial dimension in a first condition and a second radial dimension in a second condition. The second radial dimension is larger than the first radial dimension. The prong(s) is configured to permit the plug to deliver energy to the surgical instrument in the first condition and configured to inhibit the plug from delivering energy to the surgical instrument in the second condition. The prong(s) mechanically transitions from the first condition to the second condition upon reaching a predetermined usage threshold. The predetermined usage threshold is determined by a number of times the plug delivers energy to the surgical instrument or the amount of time the plug delivers energy to the surgical instrument.

According to some aspects of the present disclosure, the prong(s) is constructed of a smart material.

According to another aspect of the disclosure, the prong(s) includes a fin that mechanically transitions from a retracted position to an extended position. In the extended position, the fin prevents the plug from engaging the receptacle. In some embodiments, the fin is actuated by an actuating assembly. In some embodiments, the fin is biased towards the extended position and the actuating assembly severs a retaining member releasing the fin from the retracted position.

According to yet another aspect of the disclosure, the prong(s) is retained within a body of the plug. The prong(s) has a retracted position and a protruding position. In one position, the prong(s) permits the plug to engage the receptacle and receive energy from the energy source and in the other position, the prong(s) inhibits the plug from engaging the receptacle and/or receiving energy from the energy source.

According to aspects of the present disclosure, the surgical system includes an energy source and a surgical device. The energy source is configured to output energy and includes a receptacle. The surgical device is configured to deliver energy to the tissue of a patient and has a plug which engages the receptacle. The plug includes a prong which is configured to transition from a first condition to a second condition. In the first condition the prong permits the plug to engage the receptacle permitting the surgical device to receive energy from the energy source and deliver the energy the tissue. In the second condition the prong inhibits the plug from engaging the receptacle and/or inhibits the surgical device from receiving energy from the energy source. The predetermined usage threshold is determined by using differing metrics depending on the instrument and the type of use. In some embodiments, the predetermined usage threshold is measured by a safe life of the instrument. The safe life of the instrument is measured by the number of times the plug engages the receptacle, the number of times energy is output from the energy source to instrument, an amount of time which the plug is engaged with receptacle, and/or the amount of time energy is outputted from the energy source to the instrument.

According to still yet another aspect, a method for performing an electrosurgical procedure is disclosed. The method includes the steps of coupling an electrosurgical instrument to a receptacle of an energy source; energizing the electrosurgical instrument; decoupling the electrosurgical instrument; repeatedly coupling, energizing, and decoupling the electrosurgical instrument until a predetermined amount of usage is reached; and disposing of the electrosurgical instrument. In some embodiments, the predetermined amount of usage is indicated when the electrosurgical instrument will no longer physically engage the receptacle. In some embodiments, the predetermined amount of usage is indicated when the electrosurgical instrument no longer receives energy from the energy source.

BRIEF DESCRIPTION OF THE DRAWINGS

Various aspects and features of the present disclosure are described herein with reference to the drawings wherein.

DETAILED DESCRIPTION

Figure 1:
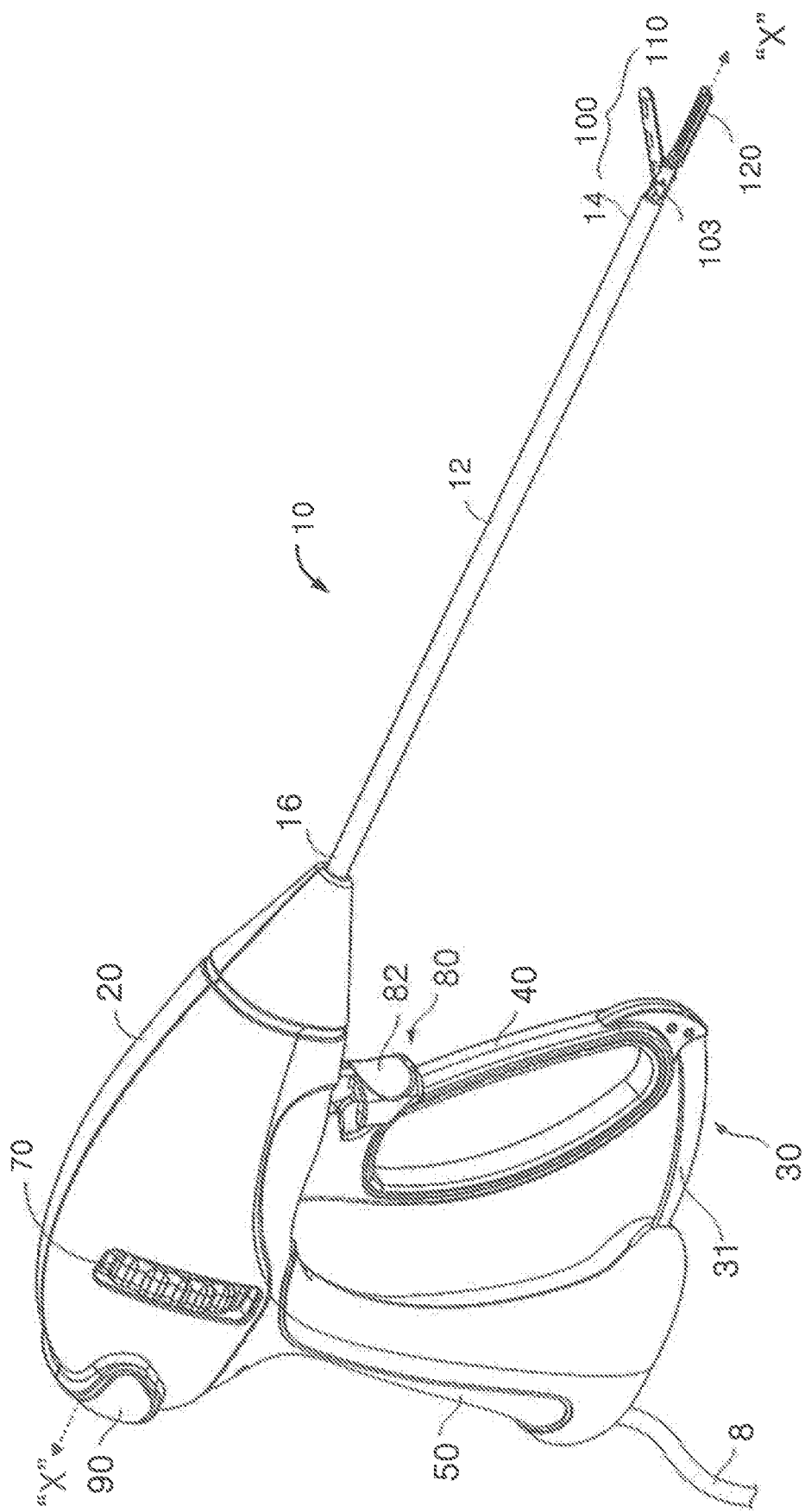
FIG. 1 is a front, side perspective view of an endoscopic surgical forceps configured for use in accordance with the present disclosure.
Figure 2:
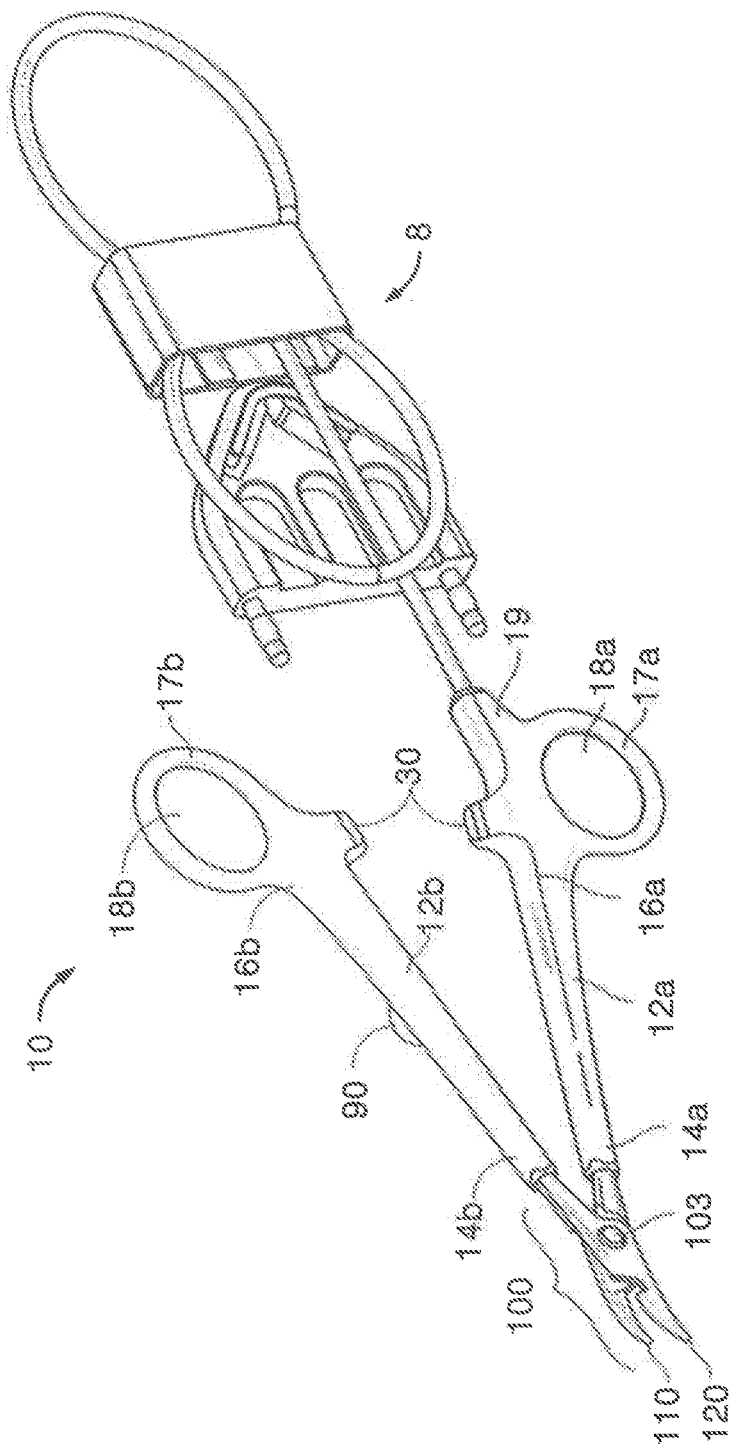
FIG. 2 is a front, side perspective view of an open surgical forceps configured for use in accordance with the present disclosure.

Referring now to the drawings, in which like reference numerals identify identical or substantially similar parts throughout the several views, FIG. 1 depicts an instrument 10 for use in connection with endoscopic surgical procedures and FIG. 2 depicts an open instrument 10' contemplated for use in connection with traditional open surgical procedures. For the purposes herein, either an endoscopic device, e.g., instrument 10, an open device, e.g., instrument 10', or any other suitable surgical device may be utilized in accordance with the present disclosure. Obviously, different electrical and mechanical connections and considerations apply to each particular type of device, however, the aspects and features of the present disclosure remain generally consistent regardless of the particular device used.

Turning now to FIG. 1, an electrosurgical instrument 10 is provided defining a longitudinal axis "X-X" and including a housing 20, a handle assembly 30, a rotating assembly 70, a trigger assembly 80, and an end effector assembly 100. Instrument 10 further includes a shaft 12 having a distal end 14 configured to mechanically engage end effector assembly 100 and a proximal end 16 that mechanically engages housing 20. Instrument 10 also includes cable 8 that connects instrument 10 to an energy source 300 (FIG. 4), e.g., an electrosurgical generator or other suitable power source. Cable 8 includes a wire (or wires) (not shown) extending therethrough that has sufficient length to extend through shaft 12 in order to provide energy to one or both of the tissue-contacting surfaces 112, 122 (FIG. 3A) of jaw members 110, 120, respectively. An activation switch 90 is provided on housing 20 and is configured to selectively supply energy to jaw members 110, 120.

With continued reference to FIG. 1, handle assembly 30 includes fixed handle 50 and a movable handle 40. Fixed handle 50 is integrally associated with housing 20 and handle 40 is movable relative to fixed handle 50. Rotating assembly 70 is rotatable in either direction about a longitudinal axis "X-X" to rotate end effector 100 about longitudinal axis "X-X." Housing 20 houses the internal working components of instrument.

Continuing with reference to FIG. 1, movable handle 40 of handle assembly 30 is ultimately connected to a drive assembly (not shown) that, together, mechanically cooperate to impart movement of jaw members 110 and 120 between a spaced-apart position and an approximated position to grasp tissue disposed between jaw members 110, 120. As shown in FIG. 1, movable handle 40 is initially spaced-apart from fixed handle 50 and, correspondingly, jaw members 110, 120 are in the spaced-apart position. Movable handle 40 is compressible from this initial position to a compressed position corresponding to the approximated position of jaw members 110, 120. In some embodiments, a knife assembly (not shown) is provided. Trigger 82 of trigger assembly 80 is operably coupled to the knife assembly (not shown) for selectively translating a knife blade (not shown) through a knife channel 115 (FIG. 3A) defined within one or both of jaw members 110, 120 to cut tissue disposed between jaw members 110, 120.

Referring now to FIG. 2, an open instrument 10' is shown including two elongated shafts 12a and 12b, each having a proximal end 16a and 16b, and a distal end 14a and 14b, respectively. Similar to instrument 10 (FIG. 1), instrument 10' is configured for use with end effector assembly 100. More specifically, end effector assembly 100 is attached to distal ends 14a and 14b of shafts 12a and 12b, respectively. As mentioned above, end effector assembly 100 includes a pair of opposing jaw members 110 and 120 that are pivotably connected about a pivot 103. Each shaft 12a and 12b includes a handle 17a and 17b disposed at the proximal end 16a and 16b thereof. Each handle 17a and 17b defines a finger hole 18a and 18b therethrough for receiving a finger of the user. As can be appreciated, finger holes 18a and 18b facilitate movement of the shafts 12a and 12b relative to one another which, in turn, pivots jaw members 110 and 120 from an open position, wherein the jaw members 110 and 120 are disposed in spaced-apart relation relative to one another, to a closed position, wherein the jaw members 110 and 120 cooperate to grasp tissue therebetween.

A ratchet assembly 30' may be included for selectively locking the jaw members 110 and 120 relative to one another at various positions during pivoting. Ratchet assembly 30' may include graduations or other visual markings that enable the user to easily and quickly ascertain and control the amount of closure force desired between the jaw members 110 and 120. Instrument 10 (FIG. 1) may also include a ratchet assembly 31 (FIG. 1) for similar purposes.

Figure 4:
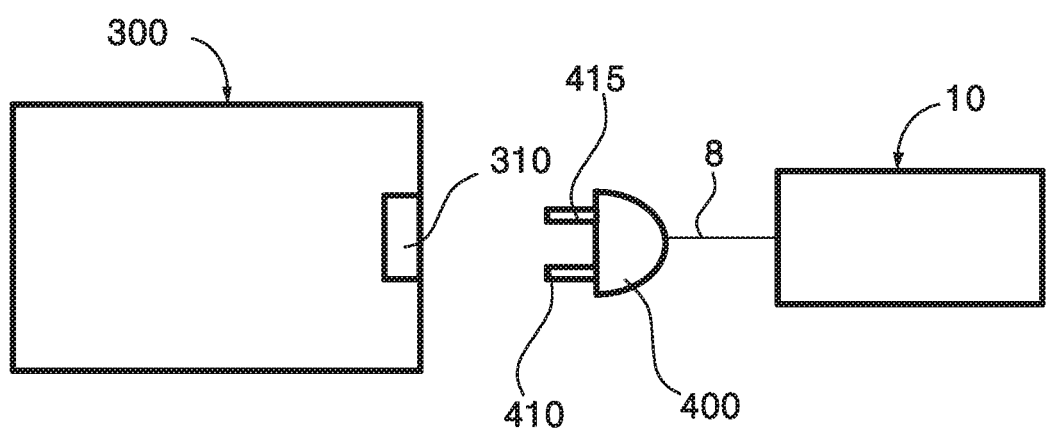
FIG. 4 is a schematic illustration of the components of a surgical system in accordance with the present disclosure.

With continued reference to FIG. 2, one of the shafts, e.g., shaft 12a, includes a proximal shaft connector 19 which is designed to connect the instrument 10' to the source of energy 300 (FIG. 4). Proximal shaft connector 19 secures an electrosurgical cable 8' to instrument 10' such that the user may selectively apply energy to jaw members 110 and 120, as needed. One of the shafts, e.g., shaft 12a, includes an activation switch 90' for selectively supplying energy to jaw members 110, 120.

Figure 3A:
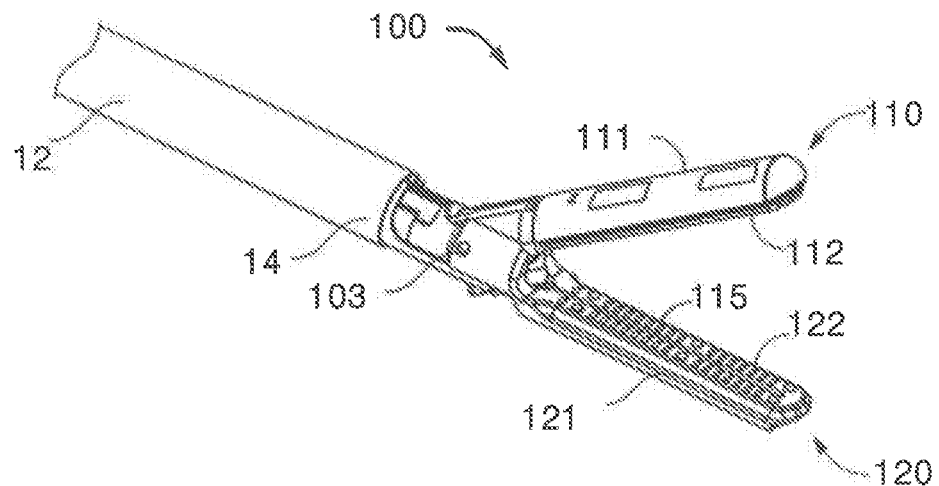
FIG. 3A is a front, side perspective view of an end effector assembly configured for use with the forceps of FIG. 1 or 2.
Figure 3B:
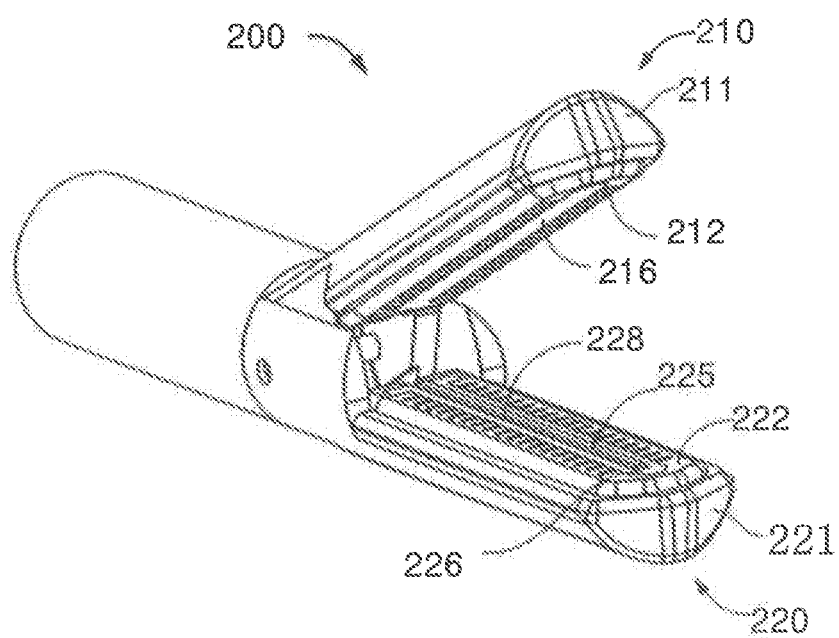
FIG. 3B is a front, side perspective view of another end effector assembly configured for use with the forceps of FIG. 1 or 2.

Referring to FIGS. 3A and 3B, end effector assemblies configured for use with instrument 10 (FIG. 1), instrument 10' (FIG. 2), or any other suitable surgical device are generally designated as end effector assemblies 100, 200, respectively. However, for purposes of simplicity, end effector assemblies 100, 200 will be described herein as configured for use with instrument 10 (FIG. 1). End effector assemblies 100, 200 are generally similar to one another except that end effector assembly 100 (FIG. 3A) is configured to permit translation of a knife blade (not shown) through knife slot(s) 115 defined within one or both of jaw members 110, 120 to dynamically cut tissue therebetween, while end effector assembly 200 (FIG. 3B) includes an electrical cutting assembly 225 configured to conduct energy through tissue to statically cut tissue grasped between jaw members 210, 220. Each of end effector assemblies 100, 200 will be described, in turn, below.

With reference to FIG. 3A, each of jaw members 110, 120 of end effector assembly 100 includes an outer insulative jaw housing 111, 121 and an electrically-conductive tissue-contacting surface 112, 122, respectively. Tissue-contacting surfaces 112, 122 are electrically coupled to activation switch 90 (FIG. 1) and the source of energy 300 (FIG. 4), e.g., via the wires (not shown) extending from cable 8 (FIG. 1) through instrument (FIG. 1), such that energy may be selectively supplied to tissue-contacting surface 112 and/or tissue-contacting surface 122 and conducted therebetween and through tissue disposed between jaw members 110, 120 to treat, e.g., seal, tissue. End effector assembly 100 is designed as a unilateral assembly, e.g., jaw member 120 is fixed relative to shaft 12 and jaw member 110 and is movable about pivot 103 relative to shaft 12 and fixed jaw member 120. However, end effector assembly 100 may alternatively be configured as a bilateral assembly, i.e., where both jaw member 110 and jaw member 120 are movable about a pivot 103 relative to one another and to shaft 12. A knife channel 115 extends longitudinally through one (or both) jaw members 110, 120, e.g., jaw member 110, to facilitate reciprocation of a knife blade (not shown) between jaw members 110, 120 to cut tissue disposed therebetween, e.g., upon actuation of trigger 82 of trigger assembly 80 (see FIG. 1). The knife blade (not shown) that is configured to translate through knife channel 115 and between jaw members 110, 120 may be configured for mechanical cutting, or may be energizable, e.g., electrically coupled to the source of energy 300 (FIG. 4) via one or more wires (not shown) of cable 8 (FIG. 1), for electromechanically cutting tissue.

Referring to FIG. 3B, similar to end effector assembly 100 (FIG. 3A), jaw members 210, 220 of end effector assembly 200 each include an outer insulative jaw housing 211, 221 and an electrically-conductive tissue-contacting surface 212, 222, respectively. Tissue-contacting surfaces 212, 222 are electrically coupled to activation switch 90 (FIG. 1) and source of energy 300 (FIG. 4), e.g., via wires (not shown) extending from cable 8 (FIG. 1) through instrument 10 (FIG. 1), for selectively supplying energy to tissue-contacting surface 212 and/or tissue-contacting surface 222 to treat, e.g., seal, tissue, in a first mode of operation. End effector assembly 200 is designed as a unilateral assembly, although end effector assembly 200 may alternatively be configured as a bilateral assembly. One of the jaw members 210, 220 of end effector assembly 200, e.g., jaw member 220, includes an electrical cutting assembly 225 disposed within a longitudinal slot extending along tissue-contacting surface 222 and jaw member 220. Electrical cutting assembly 225 includes an insulating member 226 and a cutting electrode 228. Insulating member 226 is interdisposed between cutting electrode 228 and tissue-contacting surface 222 to electrically insulate cutting electrode 228 and tissue-contacting surface 222 from one another. Cutting electrode 228 is electrically coupled to activation switch 90 (FIG. 1) and the source of energy 300 (FIG. 4), e.g., via one or more wires (not shown), for selectively supplying energy to cutting electrode 228 for conduction through tissue and to either or both of tissue-contacting surfaces 212, 222 to electrically or electromechanically cut tissue in a second mode of operation. An insulating member 216 disposed within a longitudinal slot extending along tissue-contacting surface 212 of jaw member 210 is provided to oppose cutting electrode 228.

Now referring to FIG. 4, a surgical system 1000 provided in accordance with the present disclosure and configured for use with instrument 10 (see also FIG. 1) is shown. System 1000 generally includes an energy source 300 having a receptacle 310 and an instrument, e.g., instrument 10, having a plug 400 disposed at the free end of cable 8. Plug 400 is configured to selectively engage receptacle 310 to operably couple instrument 10 and the energy source 300 to one another. Plug 400 includes one or more prongs 410. Plug 400 may include one or more fixed prongs 415.

Prong 410 is configured to mechanically transition from a first condition to a second condition. In the first condition, prong 410 permits plug 400 to engage receptacle 310 and receive energy from the energy source 300. In the second condition, prong 410 inhibits plug 400 from engaging receptacle 310 and/or receiving energy from energy source 300. Prong 410 is configured as a limited-use component which, in turn, renders instrument 10 a limited-use device. More specifically, the mechanical transition of prong 410 may be configured to occur after a predetermined usage threshold, e.g., pre-determined number of uses or pre-determined usage time, is reached, thereby rendering instrument 10 inoperable.

In some embodiments, the predetermined usage threshold is determined by using differing metrics depending on the limited-use device and/or the type of limited-use. For single-use type disposable instruments the predetermined usage threshold is once, one use, or a single use. For reusable type instruments the predetermined usage threshold is measured by a safe life of the device. The safe life of the device may be measured by one or more of the number of times the plug 400 engages receptacle 310, the number of times energy is outputted from the energy source 300 to instrument 10, an amount of time which plug 300 is engaged with receptacle 310, or the amount of time energy is outputted from the energy source 300 to instrument 10. Other suitable usage thresholds and/or configurations for determining the end of the safe life of a device are also contemplated. Various embodiments of prongs and/or plugs of surgical instruments configured to implement a pre-determined usage threshold by mechanically transitioning between a first condition and a second condition are detailed below with respect to FIGS. 5A-11B.

Figure 5A:
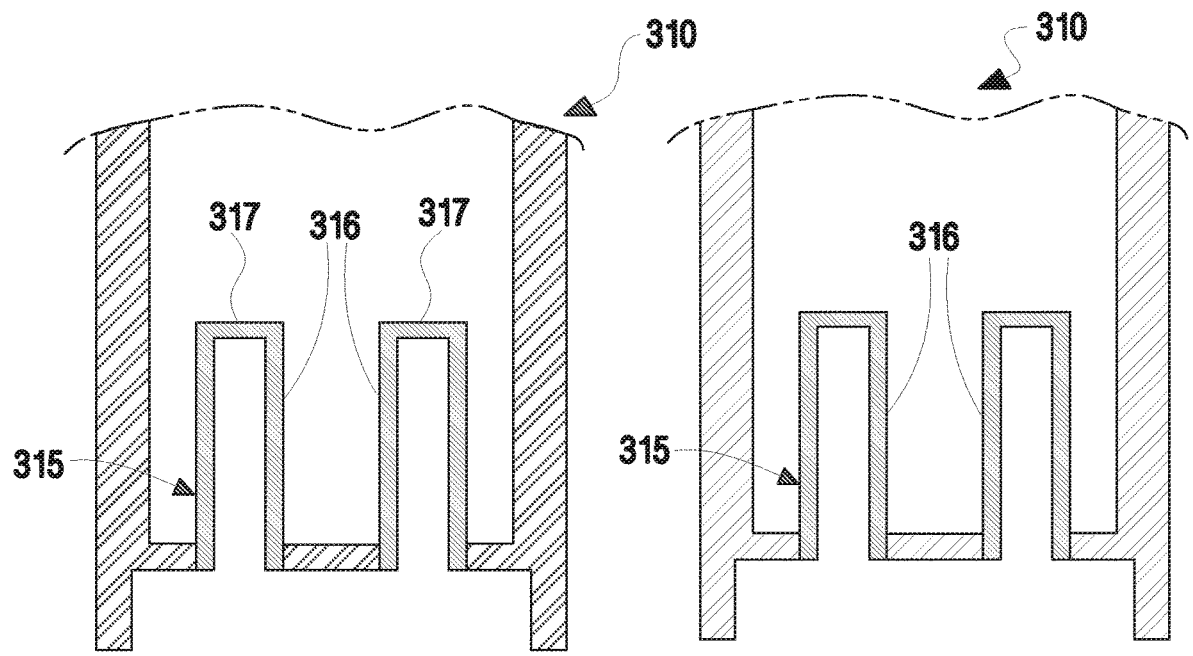
FIG. 5A is a top, cross-sectional view of a receptacle and plug in accordance with the present disclosure, shown in a first condition.
Figure 5B:
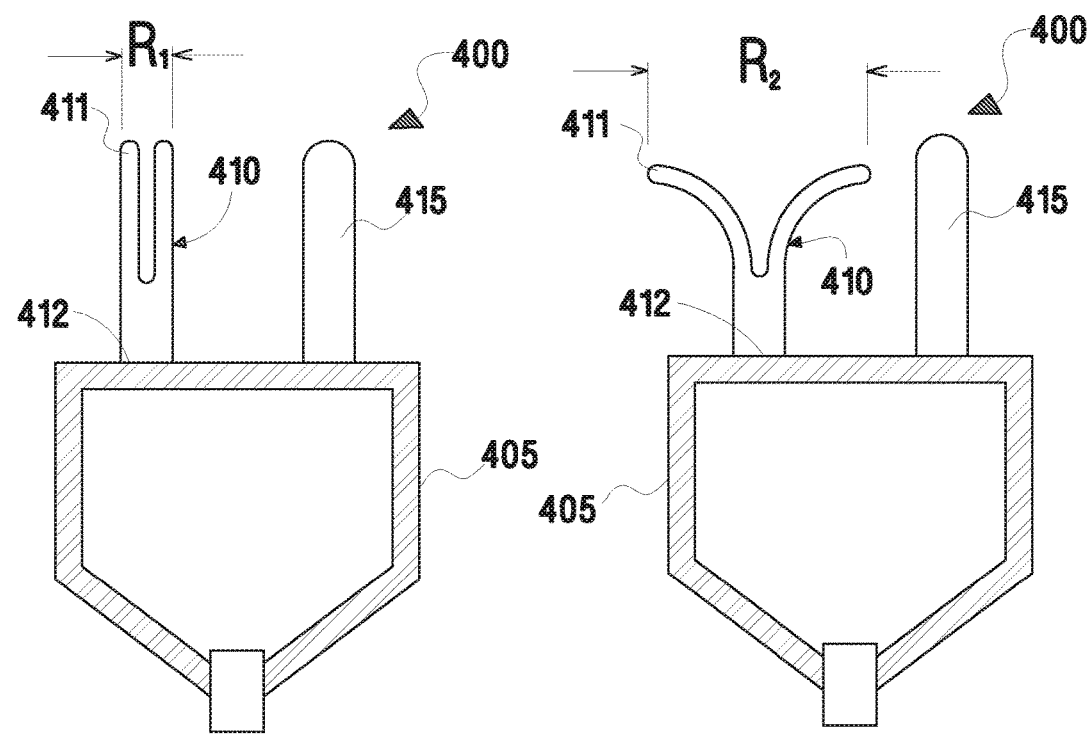
FIG. 5B is a top, cross-sectional view of the receptacle and plug of FIG. 5A, shown in a second condition.

Referring now to FIGS. 5A and 5B, receptacle 310 of energy source 300 (FIG. 4) includes one or more receptacle slots 315. Each receptacle slot 315 includes sidewalls 316 and an endwall 317. In some embodiments, in the first condition (FIG. 5A), prong 410 defines a first radial dimension $R_1$ which permits prong 410 of plug 400 to engage one of the receptacle slots 315 of receptacle 310, thus permitting energy to be transmitted from energy source 300 to instrument 10 (see FIG. 4). In the second condition (FIG. 5B), prong 410 defines a second radial dimension $R_2$ that inhibits prong 410 of plug 400 from engaging receptacle slots 315 of receptacle 310, thereby inhibiting the transmission of energy from the energy source 300 to instrument 10 (see FIG. 4) via plug 400 and, thus, rendering instrument 10 (see FIG. 4) unusable. The particular configuration of prong 410 and its transition from the first condition to the second condition are described below.

Continuing with reference to FIGS. 5A and 5B, prong 410 includes a pair of tip portions 411 (although greater or fewer than two tip portions 411 are also contemplated) and a base 412. Each tip portion 411 has a first position corresponding to the first condition and a second position corresponding to the second condition. In the first position, tip portions 411 are disposed in a relatively close-together, substantially parallel orientation to define the first radial dimension $R_1$ of prong 410, as shown in FIG. 5A. In the second position, tip portions 411 deflect outwardly, e.g., in opposing directions, relative to one another such that the free ends of tip portions 411 define the second radial dimension $R_2$, as shown in FIG. 5B. Second radial dimension $R_2$ is larger than first radial dimension $R_1$. More specifically, second radial dimension $R_2$ is greater than the distance between receptacle sidewalls 316 such that prong 410 is inhibited from engaging within receptacle slot 315. In some embodiments, the transition from the first condition to the second condition occurs while plug 400 is engaged with receptacle 310. When the transition from the first position to the second position occurs while plug 400 is engaged with receptacle 310, tip portions 411 are biased against sidewalls 316 of receptacle slot 315 allowing plug 400 to remain engaged to receptacle 310 but inhibiting reengagement once plug 400 disengages receptacle 310.

In some embodiments, one or more portions of prong 410 are made of a smart material. In some embodiments, only tip portions 411 of prong 410 are made of a smart material. In certain embodiments, the smart material is a shape memory alloy, for example Nitinol. In other embodiments, the smart material may be a light-induced smart polymer, an electro-active smart polymer, a magnetic shape memory alloy, or other suitable smart material. In such embodiments wherein prong 410 (or a portion thereof) is made of a smart material, prong 410 may be configured to transition from the first condition to the second condition upon application of one or more of the above transforming energies to prong 410. For example, in embodiments where prong 410 (or a portion thereof) is constructed of Nitinol (or other suitable temperature-dependent smart material), the transforming energy may be heat energy generated from the transmission of energy between energy source 300 and device 10 (FIG. 4) through prong 410 and plug 400. Alternatively, in embodiments where prong 410 (or a portion thereof) is constructed of a magnetic shape memory alloy, the transforming energy may be a magnetic field generated in receptacle 310 and/or plug 400.

Figure 6A:
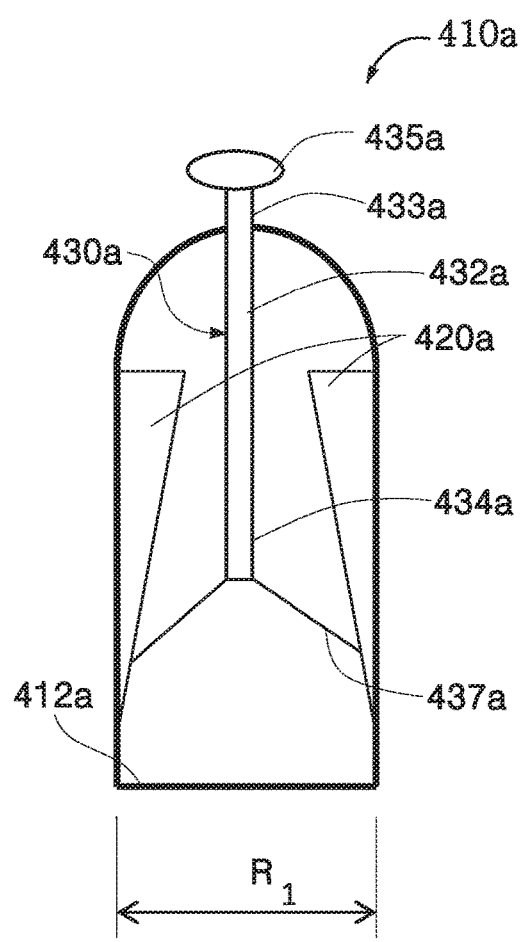
FIG. 6A is a top, cross-sectional view of a prong of a plug in accordance with the present disclosure, shown in the first condition.
Figure 6B:
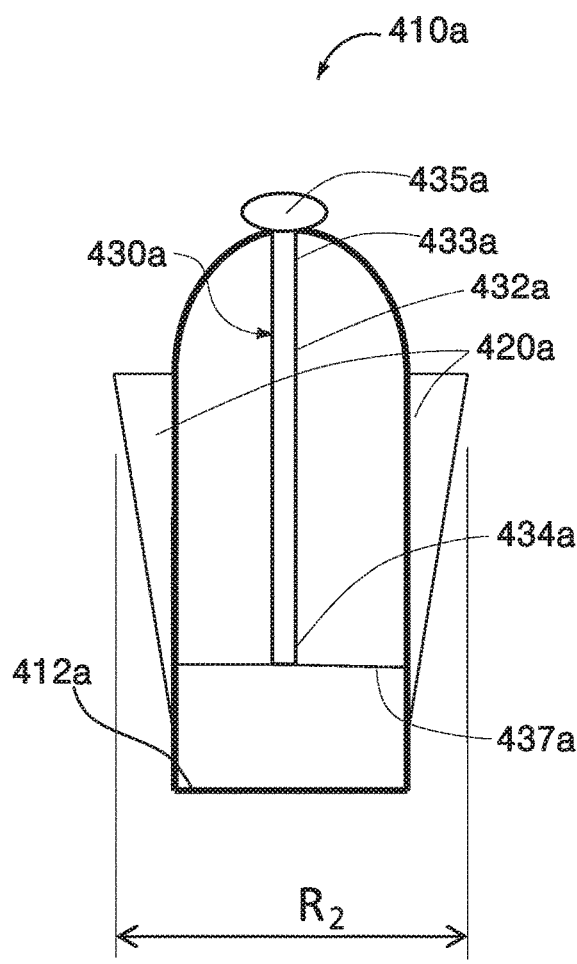
FIG. 6B is a top, cross-sectional view of the prong of FIG. 6A, shown in the second condition.

Referring now to FIGS. 6A and 6B, another embodiment of a prong 410a provided in accordance with the present disclosure is transitionable between a first condition (FIG. 6A) and a second condition (FIG. 6B) is shown. Prong 410a includes one or more fins 420a, each having a retracted position corresponding to the first condition illustrated in FIG. 6A and an extended position corresponding to the second condition illustrated in FIG. 6B. In the first condition a first radial dimension $R_1$ of prong 410a is defined by the radial dimension of base 412a of prong 410a. In the second condition a second radial dimension $R_2$ of prong 410a is defined by the one or more fins 420a which, as shown in FIG. 6B, extend outwardly beyond the radial dimension of base 412a. The particular configuration of prong 410a and its transition from the first condition to the second condition are described below.

Continuing to refer to FIGS. 6A and 6B, the one or more fins 420a are actuated by an actuation assembly 430a. Actuation assembly 430a transitions each fin 420a from the retracted position to the extended position. Actuation assembly 430a includes a shaft 432a having a distal portion 433a and a proximal portion 434a. In some embodiments, distal portion 433a includes an end feature 435a, e.g., a cap, a slot, a rib, or a high friction surface. End feature 435a may cooperate with receptacle 310 to transition prong 410a from the first condition to the second condition. In certain embodiments, end feature 435a prevents shaft 432a from fully engaging (or being fully disposed within) prong 410a as shown in FIG. 6B.

With continued reference to FIGS. 6A and 6B, actuating assembly 430a has an unactuated state corresponding to the first condition and an actuated state corresponding to the second condition. Actuating assembly 430a also includes actuating arms 437a coupled to proximal portion 434a of shaft 432a. In the unactuated state, distal portion 433a of shaft 432a extends from the end of prong 410a as shown in FIG. 6A. In the actuated state, distal portion 433a is substantially disposed within prong 410a as shown in FIG. 6B. Actuation assembly 430a is transitioned from the unactuated state to the actuated state when prong 410a engages one of the receptacle slots 315. More specifically, upon insertion of prong 410a into engagement within one of the receptacle slots 315 of receptacle 310, distal portion 433a of shaft 432a contacts and is urged distally via endwall 317 of receptacle slot 315 transitioning actuation assembly 430a from the unactuated state to the actuated state. In certain embodiments where the distal portion 433a of shaft 432a includes one or more end features 435a, shaft 432a may contact endwall 317 of receptacle slot 315 as prong 410a engages receptacle slot 315 transitioning actuation assembly 430a from the unactuated to the actuated state. Each actuation arm 437a is operatively associated with a respective fin 420a. When actuation assembly 430a transitions from the unactuated state to the actuated state, each actuating arm 437a transitions a respective fin 420a from the retracted position to the extended position. In some embodiments, shaft 432a pushes a portion of each actuation arm 437a towards base 412a of prong 410a as shown by FIGS. 6A and 6B. In certain embodiments, when fin 420a transitions from the retracted position to the extended position while prong 410a is engaged within receptacle slot 315, fin 420a is biased against sidewalls 316 of receptacle slot 315 allowing prong 410a to remain engaged within receptacle slot 315 but inhibiting prong 410a from re-engaging receptacle slot 315 once prong 410a is disengages receptacle slot 315. Arms 437a may be coupled between shaft 432a and fins 420a via any suitable mechanisms including, but not limited to, linkages, pivots, hinges, flexible couplings etc.

Figure 7A:
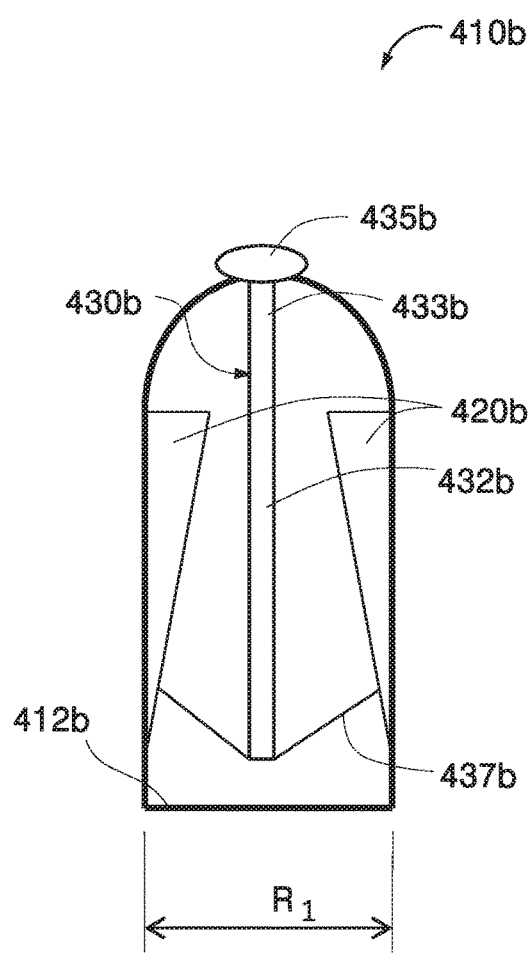
FIG. 7A is a top, cross-sectional view of another prong of a plug in accordance with the present disclosure, shown in the first condition.
Figure 7B:
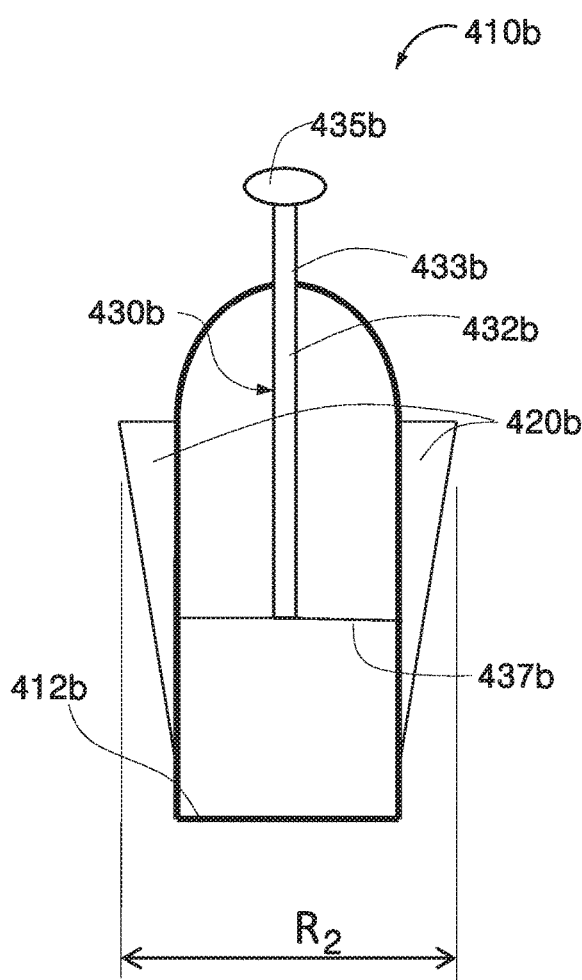
FIG. 7B is a top, cross-sectional view of the prong of FIG. 7A, shown in the second condition.
Figure 7C:
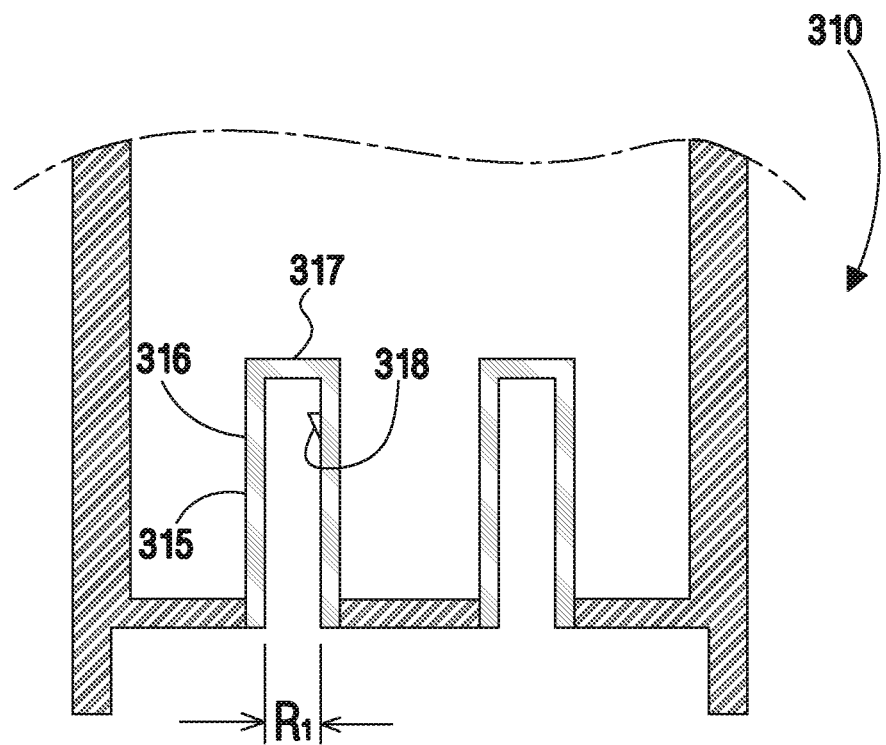
FIG. 7C is a top, cross-sectional view of a receptacle configured to accept the prong of FIGS. 7A and 7B.

Referring now to FIGS. 7A-7C, another embodiment of a prong 410b, similar to prong 410a (FIGS. 6A and 6B), provided in accordance with the present disclosure is shown having a first condition (FIG. 7A) and a second condition (FIG. 7B). For purposes of brevity, only the differences between prong 410b and prong 410a (FIGS. 6A and 6B) are described in detail below.

In the unactuated state of prong 410b, distal portion 433b of shaft 432b is substantially engaged or substantially disposed within prong 410b as shown in FIG. 7A. In the actuated state, distal portion 433b of shaft 432b is at least partially extended from the end of prong 410b as shown in FIG. 7B. When prong 410b is removed from receptacle slot 315 of receptacle 310, an actuating structure 318 in receptacle slot 315 engages end feature 435b transitioning actuation assembly 430b from the unactuated state to the actuated state. Actuating structure 318 (FIG. 7C) may a rib, a detent, a high friction surface, or any other known mechanical interface or releasably engaging end feature 435b. When actuation assembly 430b is transitioned from the unactuated state to the actuated state, shaft 432b is urged distally such that actuating arms 437b are drawn away from base 412b of prong 410b extending each of the fins 420b from prong 410b.

Figure 8A:
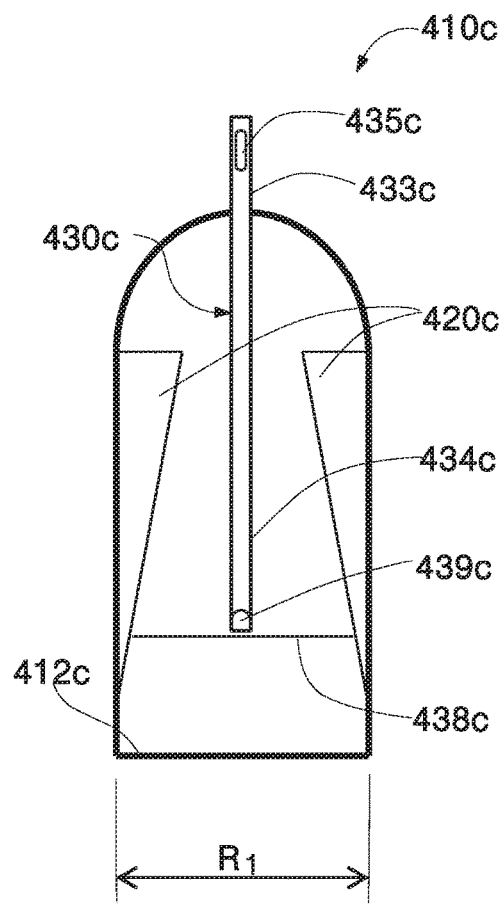
FIG. 8A is a top, cross-sectional view of another prong of a plug in accordance with the present disclosure, shown in the first condition.
Figure 8B:
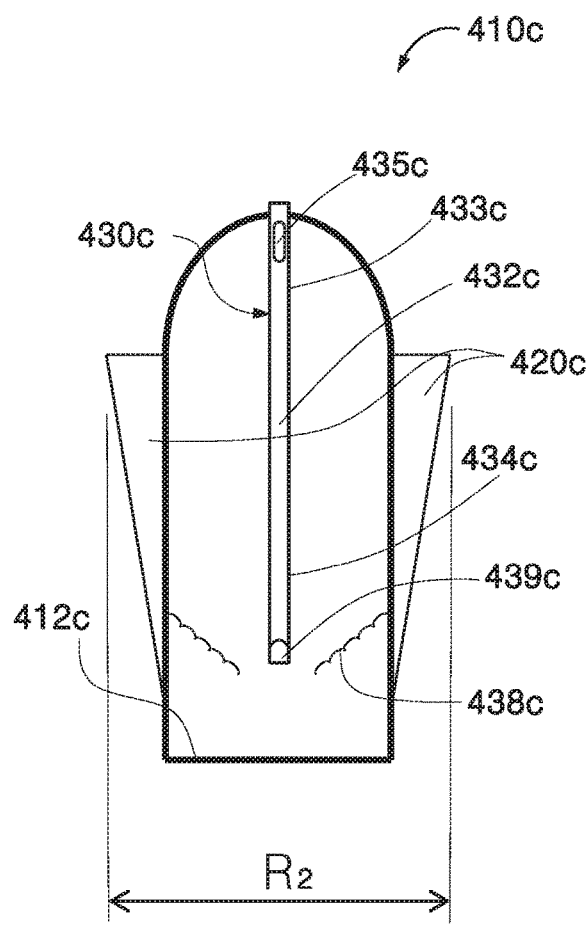
FIG. 8B is a top, cross-sectional view of the prong of FIG. 8A, shown in the second condition.

FIGS. 8A and 8B illustrate another embodiment of a prong 410c provided in accordance with the present disclosure and configured to transition from a first condition (FIG. 8A) and a second condition (FIG. 8B). Prong 410c is similar to prong 410a (FIGS. 6A and 6B) and, thus, only the differences between prong 410c and prong 410a (FIGS. 6A and 6B) are described in detail below for purposes of brevity.

Fin 420c of prong 410c is biased to outwardly extend radially from prong 410c. However, in the unactuated condition of prong 410c, fin 420c is retained within prong 410c by a retaining member 438c of actuation assembly 430c. Retaining member 438c may be a string, a cord, a wire, or a thin member. Proximal portion 434c of shaft 432c includes a severing member or feature 439c. Severing feature 439c may be a hook, a sharpened tip, a detent, or any other suitable structure for severing retaining member 438c. Fins 420c may be retained by the same retaining member 438c or separate retaining members 438c.

Upon insertion of prong 410c into one of the receptacle slots 315 of receptacle 310 (FIGS. 5A and 5B), the distal portion 433c of shaft 432c contacts endwall 317 of receptacle slot 315 (FIGS. 5A and 5B) urging shaft 432c towards base 412c of prong 410c such that severing member 439c severs retaining member 438c. When retaining member 438c is severed, fins 420c, being biased to the extended position, transition from the retracted position to the extended position. In certain embodiments, when retaining member 438c is severed while prong 410c is engaged with receptacle slot 315, fin 420c remains in the retracted position until prong 410c disengages receptacle slot 315.

Figure 9A:
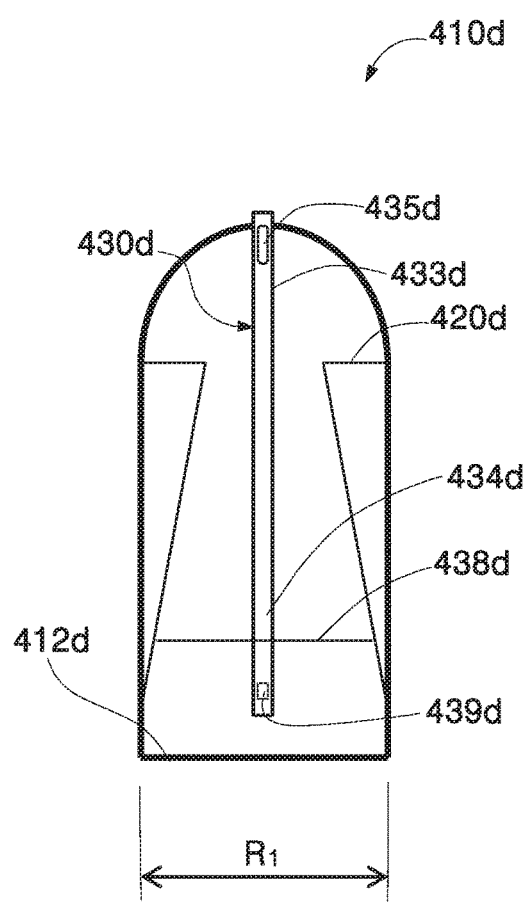
FIG. 9A is a top, cross-sectional view of another prong of a plug in accordance with the present disclosure, shown in the first condition.
Figure 9B:
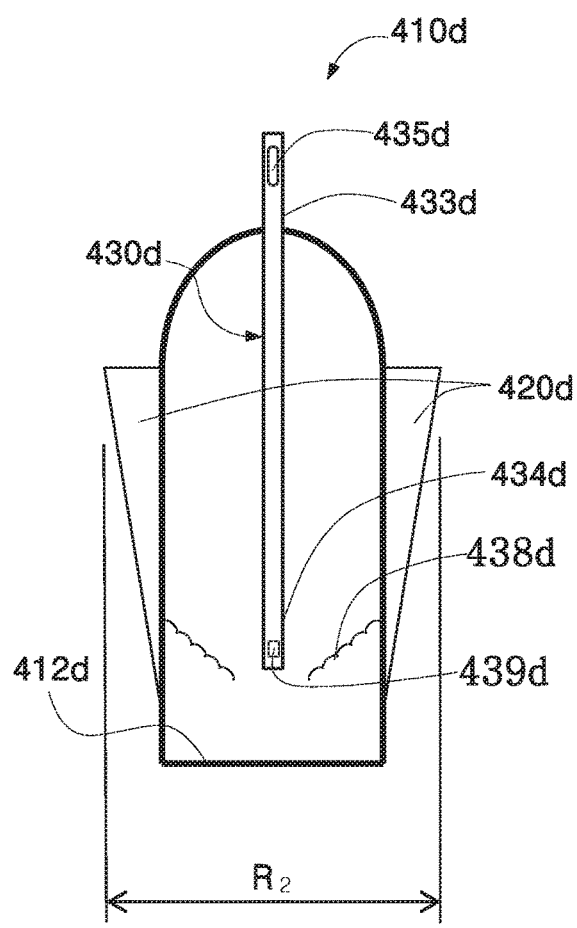
FIG. 9B is a top, cross-sectional view of the prong of FIG. 9A, shown in the second condition.

Referring now to FIGS. 9A and 9B, another embodiment of a prong 410d provided in accordance with the present disclosure and configured to transition from a first condition (FIG. 9A) to a second condition (FIG. 9B) is shown. Prong 410d is similar to prong 410c (FIGS. 8A and 8B) and, thus, only the differences between prong 410d and prong 410c (FIGS. 8A and 8B) are described in detail below for purposes of brevity. Prong 410d is configured for use with a receptacle slot 315 having an actuating structure 318 as described above with respect to FIG. 7C.

Fin 420d of prong 410d is biased to the extended position and is retained by a retaining member 438d in a similar fashion as described above. In the unactuated state, the distal portion 433d of shaft 432d is substantially engaged or substantially disposed within prong 410d as shown in FIG. 9A. In the actuated state, distal portion 433d of shaft 432d is at least partially extended from the free end of prong 410d as shown in FIG. 9B. When shaft 432d is drawn away from base 412d of prong 410d, e.g., via actuating structure 318 of receptacle slot 315 (FIG. 7C) during disengagement of prong 410d, severing member 439d severs retaining member 438d. When retaining member 438d is severed, fins 420d, being biased to the extended position, transition from the retracted position to the extended position.

Figures 10A, 10B:
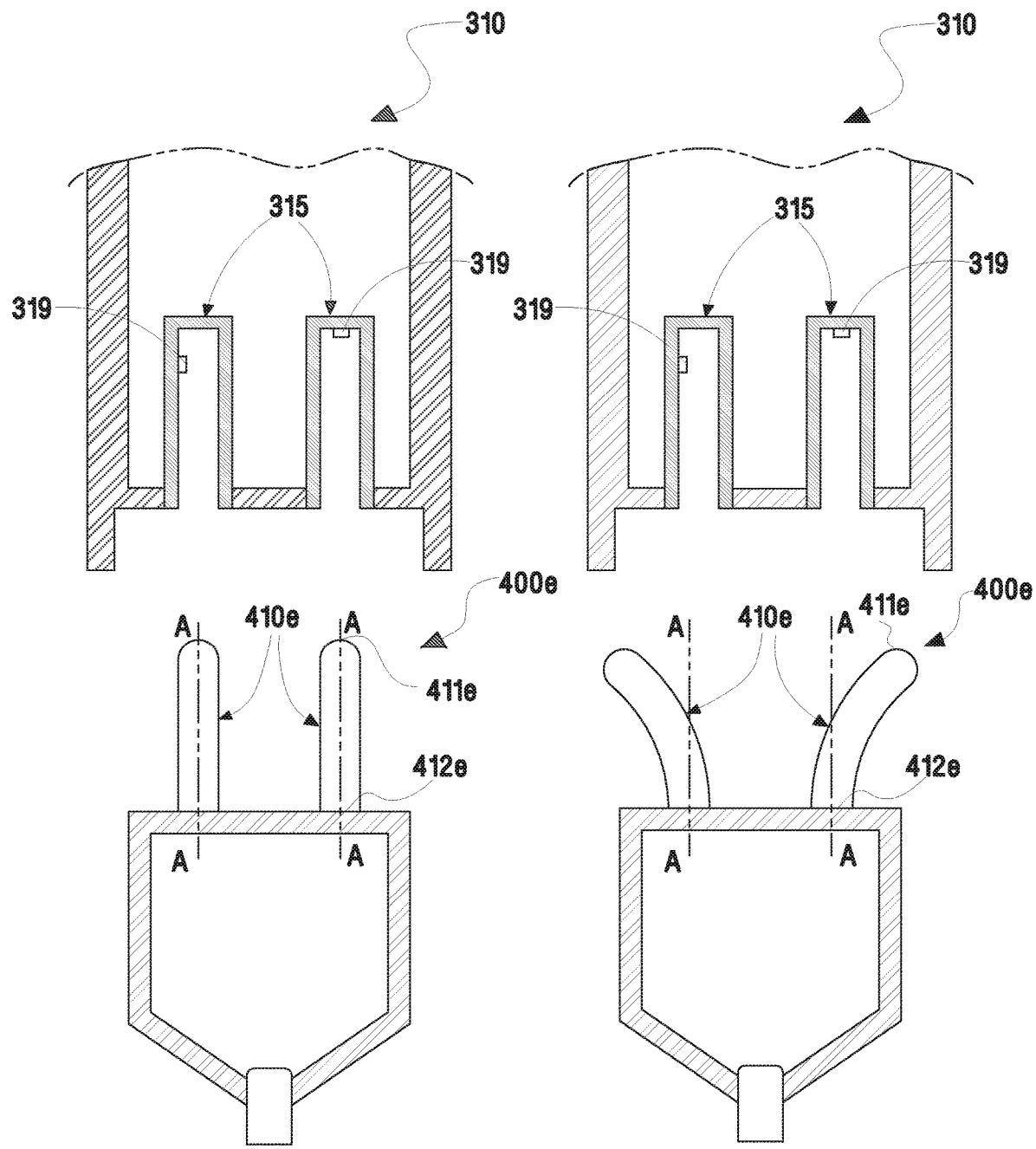
FIG. 10A is a top, cross-sectional view of another plug in accordance with the present disclosure, shown in the first condition.
FIG. 10B is a top, cross-sectional view of the plug of FIG. 10A, shown in the second condition.

Referring now to FIGS. 10A and 10B, another embodiment of a plug 400e including one or more prongs 410e is shown. Each prong 410e defines a longitudinal axis "A-A" and includes a prong tip 411e and a base 412e. Each prong 410e has a first condition and a second condition. In one condition, prong tip 411e and base 412e are aligned along longitudinal axis "A-A" as shown in FIG. 10A and in the other condition prong tip 411e and/or base 412e are offset relative to longitudinal axis "A-A" as shown in FIG. 10B. In some embodiments when two or more prongs 410e are provided, the prong tips 411e and/or bases 412e may be configured to move in different directions relative to one another. In some embodiments, the different directions are opposing directions. In certain embodiments, receptacle slot 315 includes a sensor 319 which is configured to verify that prong tip 411e and/or base 412e of prong 410e is in a required position before energy source 300 transmits energy to instrument 10 (see FIG. 4). When either prong tip 411e and/or base 412e are not in the required position, energy source 300 is inhibited from transmitting of energy to instrument 10 (see FIG. 4) via prong 410e. In particular embodiments, one or more portions of prong 410e are made from a smart material as discussed above with respect to prong 410 (FIGS. 5A-5B).

Figures 11A, 11B:
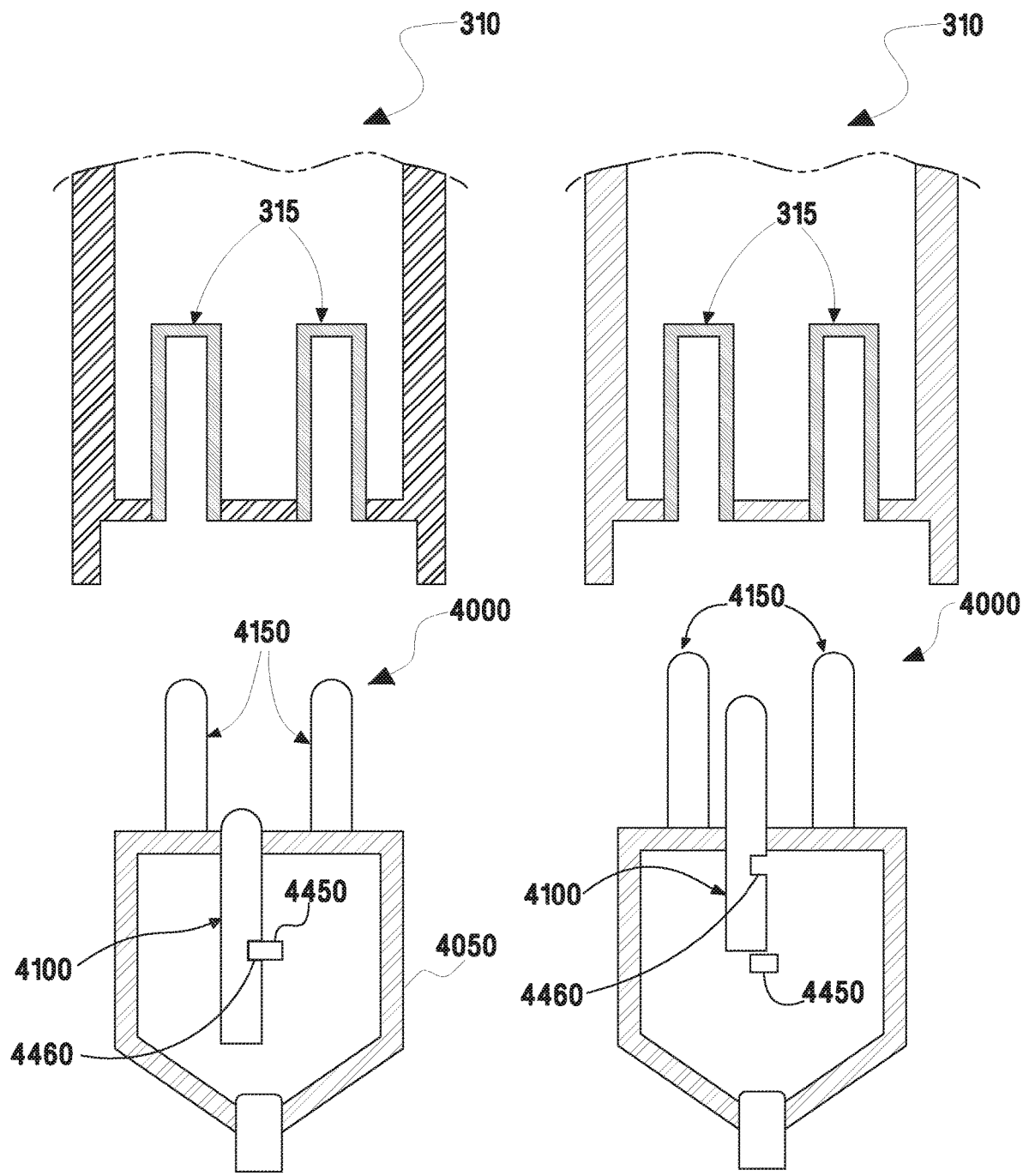
FIG. 11A is a top, cross-sectional view of another plug in accordance with the present disclosure, shown in the first condition.
FIG. 11B is a top, cross-sectional view of the plug of FIG. 11A, shown in the second condition.

FIGS. 11A and 11B illustrate another embodiment of a plug 4000 provided in accordance with the present disclosure including two or more fixed prongs 4150 configured to engage corresponding apertures or receptacle slots 315 defined within receptacle 310 of energy source 300 (FIG. 4). Plug 4000 further includes a movable prong 4100. In the first condition (FIG. 11A), movable prong 4100 is retracted within body 4050 of plug 4000 to permit the two or more fixed prongs 4150 of plug 4000 to be fully inserted into and engaged within receptacle slots 315 of receptacle 310, thus permitting energy to be transmitted from energy source 300 to instrument 10 (see FIG. 4). In the second condition (FIG. 11B), movable prong 4100 extends from body 4050 of plug 4000 in a similar direction as fixed prongs 4150 to inhibit the two or more fixed prongs 4150 of plug 4000 from engaging or being disposed within receptacle slots 315 of receptacle 310, thereby inhibiting the transmission of energy from energy source 300 to instrument 10 (see FIG. 4) via plug 4000. In some embodiments, movable prong 4100 is resiliently retractable into body 4050 in the first condition and locked in the protruding position relative to body 4050 in the second condition. In certain embodiments, a locking mechanism 4450 inhibits prong 4100 from transitioning between the protruding position and the retracting position after a pre-determined number of resilient retractions. Locking mechanism 4450 may lock by sliding or rotating from an unlocked position to a locked position. In particular embodiments, locking mechanism 4450 engages a corresponding locking structure 4460 of movable prong 4100. Locking structure 4460 may be a tab, a detent, a clip, etc. In some embodiments, movable prong 4100 includes the locking mechanism 4450 while body 4050 of plug 4000 includes the locking structure 4460.

Referring again to FIG. 4, according to the present disclosure, methods of performing surgical procedures are also provided. Such methods include coupling plug 400 of instrument 10 to receptacle 310 of energy source 300; energizing instrument 10; decoupling plug 400 from receptacle 310; repeatedly coupling, energizing, and decoupling instrument 10 until a predetermined amount of usage is reached; and disposing of instrument 10. Plug 400 may incorporate any of the above-described prongs 410, 410a, 410b, 410c, 410d, or 410e, or may be configured similar to plug 4000, each of which has been described in detail above (see FIGS. 5A-11B). The predetermined amount of usage can be indicated by plug 400 no longer being capable of engaging receptacle 310 to receive energy from the energy source 300. In some embodiments, the predetermined amount of usage is indicated when plug 400 will no longer physically engage receptacle 310. In certain embodiments, the predetermined amount of usage is indicated when plug 400 no longer receives energy from energy source 300.

From the foregoing and with reference to the various figure drawings, those skilled in the art will appreciate that certain modifications can also be made to the present disclosure without departing from the scope of the same. While several aspects and embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular aspects and embodiments. Those skilled in the art will envision other modifications within the scope and spirit of the claims appended hereto.

What is claimed is:

1. A surgical instrument, comprising:
    a plug including a prong having a fin, the prong transitionable from a first condition in which the fin is disposed in a retracted position such that the prong defines a first radial dimension to a second condition in which the fin transitions to an extended position such that the prong defines a second radial dimension larger than the first radial dimension,
    wherein, when the prong is disposed in the first condition, the plug is configured for engagement with a complementary receptacle defined in an energy source and, when the prong is disposed in the second condition, the prong is configured to prevent the plug from engaging the receptacle of the energy source,
    wherein the prong further includes an actuation assembly coupled to the fin, the actuation assembly transitionable between an unactuated state in which the actuation assembly retains the fin in the retracted position to an actuated state in which the actuation assembly transitions the fin to the extended position, and
    wherein the actuation assembly includes an actuating arm and a shaft, the shaft configured to longitudinally translate within the plug as the actuation assembly transitions between the unactuated state and the actuated state, wherein the actuating arm is coupled to the shaft and the fin such that as the shaft translates within the plug, the actuation arm biases the fin to the extended position such that, upon disengagement of the prong, the fin deploys to the extended position.

2. The surgical instrument according to claim 1, wherein the fin mechanically transitions from the first condition to the second condition in response to the plug disengaging the receptacle of the energy source.

3. The surgical instrument according to claim 1, wherein, upon insertion of the prong into the complementary receptacle, the actuation assembly transitions from the unactuated state to the actuated state such that as the plug disengages from the receptacle of the energy source, the fins deploy to the extended position.

4. The surgical instrument according to claim 1, wherein the actuation assembly is configured to transition from the unactuated state to the actuated state as the plug disengages the receptacle of the energy source.

5. The surgical instrument according to claim 1, wherein the shaft includes:
    a first end portion extending from a tip of the plug and including an end feature, the end feature approximated with the tip of the plug in the unactuated position and extending from the tip of the plug in the actuated position; and
    a second end portion coupled to the actuating arm.

6. The surgical instrument according to claim 1, wherein the fin is biased towards the extended position, and wherein the actuation assembly includes a retaining member and a severing member, the retaining member configured to retain the fin in the retracted position, and the severing member configured to sever the retaining member upon transitioning of the actuation assembly from the unactuated state to the actuated state, thereby permitting the fin to transition to the extended position.

7. The surgical instrument according to claim 6, wherein the severing member is spaced apart from a tip of the plug in the unactuated state and is approximated with the tip of the plug in the actuated state.

8. The surgical instrument according to claim 6, wherein the severing member is approximated with a tip of the plug in the unactuated state and is spaced apart from the tip of the plug in the actuated state.

9. A surgical system, comprising:
    an energy source configured to output energy, the energy source including a receptacle defined therein; and
    a surgical instrument configured to deliver energy to tissue, the surgical instrument including a plug configured for engagement with the receptacle to electrically couple the surgical instrument to the energy source, the plug including a prong having a fin, the prong transitionable from a first condition in which the fin is disposed in a retracted position such that the prong defines a first radial dimension and to a second condition in which the fin transitions to an extended position such that the prong defines a second radial dimension larger than the first radial dimension,
    wherein, when the prong is disposed in the first condition, the plug is configured for engagement with the receptacle defined in an energy source, and when the prong is disposed in the second condition, the prong is configured to prevent the plug from engaging the receptacle of the energy source, and
    wherein the plug includes an actuation assembly configured to transition the fin from the retracted to the extended position, and
    wherein the actuation assembly includes a plunger configured to move from an initial position defining an unactuated state of the actuation assembly and a final position defining an actuated state of the actuation assembly.

10. The system according to claim 9, wherein the plunger includes a first end portion and a second end portion, the first end portion having an end feature extending from a tip of the prong such that the end feature is spaced part from the tip in the initial position and the end feature is approximated with the tip in the final position, wherein the second end portion is coupled to the fin by an actuation arm, the actuation arm transitioning the fin between the retracted position when the actuation assembly is in the unactuated state and the extended position when the actuation assembly is in the actuated state and the prong is removed from the receptacle.

11. The system according to claim 10, wherein the second end portion includes:

a retaining member that maintains the fin in the retracted position under a bias towards the extended position; and a severing member that cuts the retaining member as the plunger moves towards the final state such that the fin is permitted to move towards the extended position.

12. The system according to claim 9, wherein the plunger includes a first end portion and a second end portion, the first end portion having an end feature that is approximated with the tip in the initial position and the end feature is spaced part from with the tip in the final position.

13. The system according to claim 12, wherein the second end portion is coupled to the fin by an actuation arm, the actuation arm transitioning the fin between the retracted position when the actuation assembly is in the unactuated state and the extended position when the actuation assembly is in the actuated state.

14. The system according to claim 12, wherein the second end portion includes:

a retaining member that maintains the fin in the retracted position under a bias towards the extended position; and a severing member that cuts the retaining member as the plunger moves towards the final state such that the fin is permitted to move towards the extended position.

* * * * *